(12) United States Patent
O'Brien et al.

(10) Patent No.: US 6,575,575 B2
(45) Date of Patent: Jun. 10, 2003

(54) MOVEABLE POWER OPERATED INSTRUMENT STAND

(75) Inventors: James J. O'Brien, Quakertown, PA (US); Edward R. Mourar, Glenmoore, PA (US)

(73) Assignee: Topcon Medical Systems, Inc., Paramus, NJ (US)

( * ) Notice: Subject to any disclaimer, the term of this patent is extended or adjusted under 35 U.S.C. 154(b) by 13 days.

(21) Appl. No.: 09/850,581

(22) Filed: May 7, 2001

(65) Prior Publication Data

US 2002/0163624 A1 Nov. 7, 2002

(51) Int. Cl.7 .................................................. A61B 3/00
(52) U.S. Cl. ....................................................... 351/245
(58) Field of Search ................................ 351/200–205, 351/246, 245, 221; 318/11; 211/1.57, 85.13

(56) References Cited

U.S. PATENT DOCUMENTS

| | | | | |
|---|---|---|---|---|
| 723,661 A | * | 3/1903 | Evans | 433/33 |
| 4,114,274 A | | 9/1978 | Jones | |
| 4,126,939 A | * | 11/1978 | Pyne, Jr. | 433/79 |
| 4,643,547 A | * | 2/1987 | Collins et al. | 351/245 |
| 5,626,322 A | * | 5/1997 | Braun | 248/274.1 |
| 5,696,574 A | * | 12/1997 | Schwaegerle | 351/245 |
| 5,717,480 A | * | 2/1998 | Brooks et al. | 351/200 |
| 5,907,387 A | * | 5/1999 | Schwaegerle | 351/200 |
| 6,022,088 A | | 2/2000 | Metzler | |
| 6,095,649 A | * | 8/2000 | Brooks et al. | 351/221 |
| 6,264,329 B1 | * | 7/2001 | Brooks et al. | 351/221 |

OTHER PUBLICATIONS

The Marco Opthalmic Instrument Stand brocure. Undated. Admitted as Prior Art by Applicant.*
Topcon IS–1000 Ophthalmic Stand brochure. Undated admitted as prior art.
Topcon OC–20T Tilt Chair brochure. Undated admitted as prior art.
Topcon IS–800 Instrument Delivery System brochure. Undated. Admitted as prior art.
Model 7750 Ophthalmic Instrument Stand brochure. Undated. Admitted as prior art.
Model 7700 Ophthalmic Instrument Stand brochure. Undated. Admitted as prior art.
Model 7800 Ophthalmic Instrument Stand brochure. Undated. Admitted as prior art.
Model 7720 Ophthalmic Instrument Stand brochure. Undated. Admitted as prior art.
The Marco Ophthalmic Instrument Stand brochure. Undated. Admitted as prior art.

* cited by examiner

Primary Examiner—Marvin M. Lateef
Assistant Examiner—John R. Sanders
(74) Attorney, Agent, or Firm—Volpe and Koenig, P.C.

(57) ABSTRACT

The present invention provides a power operated instrument stand for use, for example during eye examinations. The instrument stand has a motorized arm to aid in precise placement of instrumentation. The instrument stand also has control circuitry for room lighting levels, patient chair positioning and slit lamp operation. The instrument stand may be controlled through an attached control pad, or a remote control.

17 Claims, 8 Drawing Sheets

MOVEABLE POWER OPERATED INSTRUMENT STAND

BACKGROUND

The present invention involves an adjustable instrument stand used in patient medical treatment. More particularly, the instrument stand is adapted for use during ophthalmic procedures.

Prior known instrument stands used in ophthalmic procedures are typically manually operated units. These stands include an external housing and a weight counterbalanced arm used to support medical instrumentation. The stand requires numerous fine tuning adjustments to place the arm in a desired position relative to a seated patient. It is often necessary for a medical professional to first adjust the arm to allow a patient to be seated. The medical professional must again adjust the arm several times after the patient is seated, depending on the tests or procedures being performed. This manual positioning hampers the efficiency of the medical professionals due to varying physical attributes of patients. Additionally, smaller patients, such as children, require raised seat heights in order for the attending physician to make proper observations. Taller patients, alternatively, require a lower seat height in order to provide the attending physician a correct observational perspective. As a further hindrance to efficiency, once the patient is seated in a proper position, the physician must often leave the patient to alter room lighting levels in order to begin examination procedures. Finally, multiple manipulations of manual seats or observational equipment makes the medical professional prone to repetitive stress syndrome.

It would be desirable to have an instrument stand with power operated and automated positional adjustments for patients to speed observation times and eliminate potential repetitive stress injury. It is also desirable to provide easy access to automated control functions previously manually performed.

SUMMARY

Briefly stated, the present invention provides a power operated instrument stand for use in medical diagnosis. The instrument stand includes a housing that defines an interior space. A control signaling device is provided to control at least one of a lamp circuit, room lights, screen/mirror fixation targets, lamp circuit, a patient chair position circuit, and an arm position circuit. A controller is provided in communication with the control signaling device. The controller is connected to an electric motor, which in turn, is connected to an actuator. The actuator is connected to a motor driven arm which extends from a side opening in the housing. A sensor is placed on the motor driven arm and is connected to the controller. The sensor is adapted to stop movement of at least one of the motor driven arm and the patient chair upon contact with an object.

BRIEF DESCRIPTION OF THE DRAWINGS

The foregoing summary as well as the following detailed description of the preferred embodiments of the invention will be better understood when read in conjunction with the appended drawings. It should be understood, however, that the invention is not limited to the precise arrangements and instrumentalities shown.

DETAILED DESCRIPTION OF THE PREFERRED EMBODIMENTS

Figure 1:
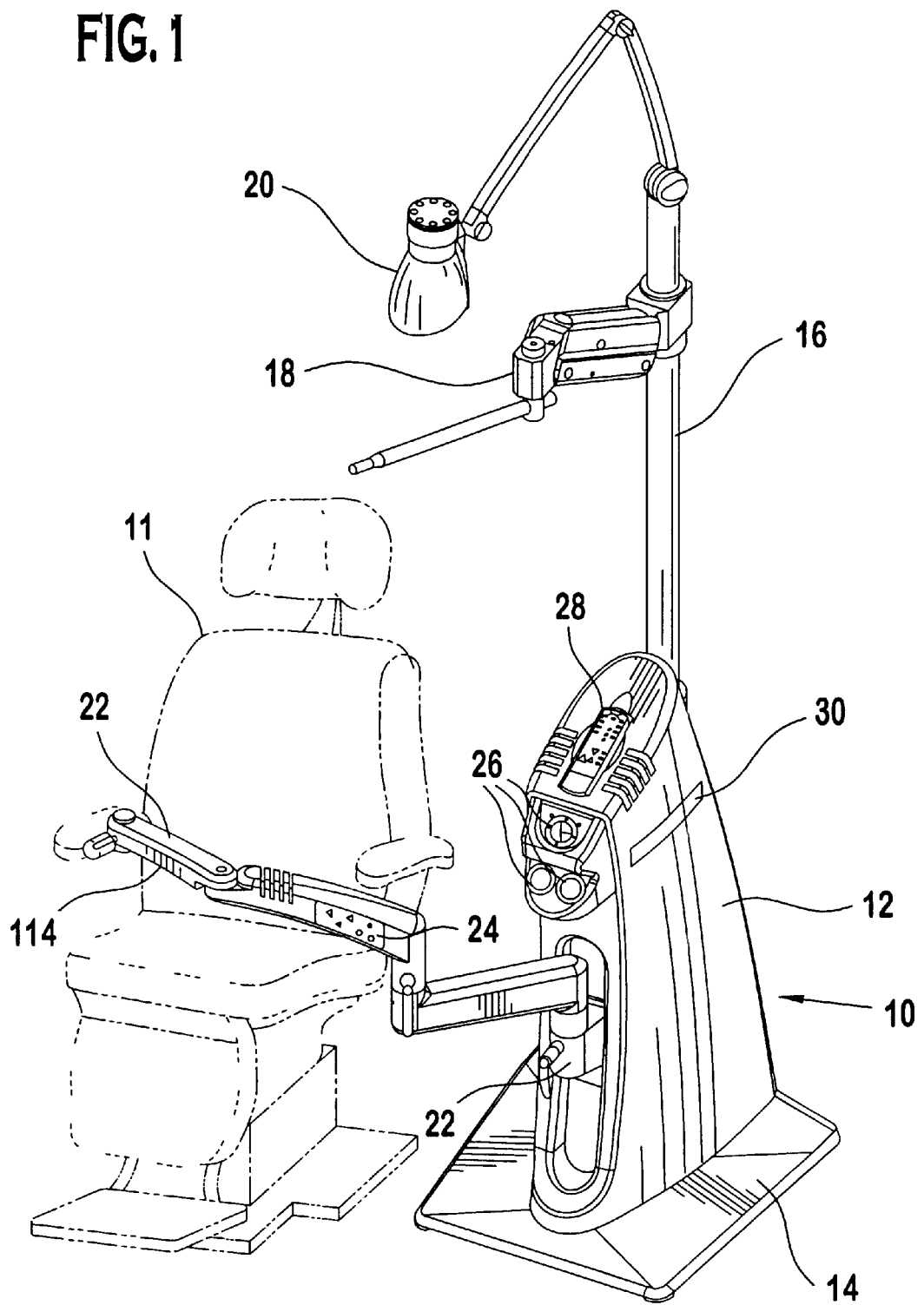
FIG. 1 is a perspective view of an instrument stand with a motorized arm in accordance with the present invention.

Referring now to FIG. 1, a perspective view of a power operated instrument stand 10 with a motorized arm 22 in accordance with the present invention is shown. The instrument stand 10 is illustrated in conjunction with a patient chair 11, shown in broken lines, which may be a power raise and tilt chair for ophthalmic procedures. An external housing 12 defines an interior space in which electrical and mechanical components of the stand 10 are located. The external housing 12 is located on a base 14. The base 14 is adapted to be used on a floor, and includes a non-skid surface to prevent movement of the instrument stand 10. Preferably, the base 14 is made of cast iron to provide weight for stability. However, other materials may be used if desired.

An instrument support pole 16 extends upwardly from the external housing 12. The instrument support pole 16 preferably includes a lamp attachment 20, and a refractor arm 18. Additional equipment may also be connected to the instrument support pole 16.

A motorized arm 22 extends from the external housing 12 to provide support for instruments to be used during patient examination, for example, during ophthalmic procedures. The motorized arm 22 is controlled by the user through a control signaling device, which is adapted to control at least one of, and preferably each of a slit-lamp circuit, a positioning circuit for the chair 11, and the positioning circuit for the motorized arm 22. The control signaling device is preferably comprised of a first input signaling device formed from a membrane switch control pad 24, shown in detail in FIGS. 6 and 8. The control signaling device preferably also comprises a remote control 28, which may control the same or fewer functions. While the preferred embodiment of the instrument stand 10 includes both the membrane switch control pad 24 and the remote control 28, those skilled in the art will understand from the present disclosure that only one control is required.

Figure 5:
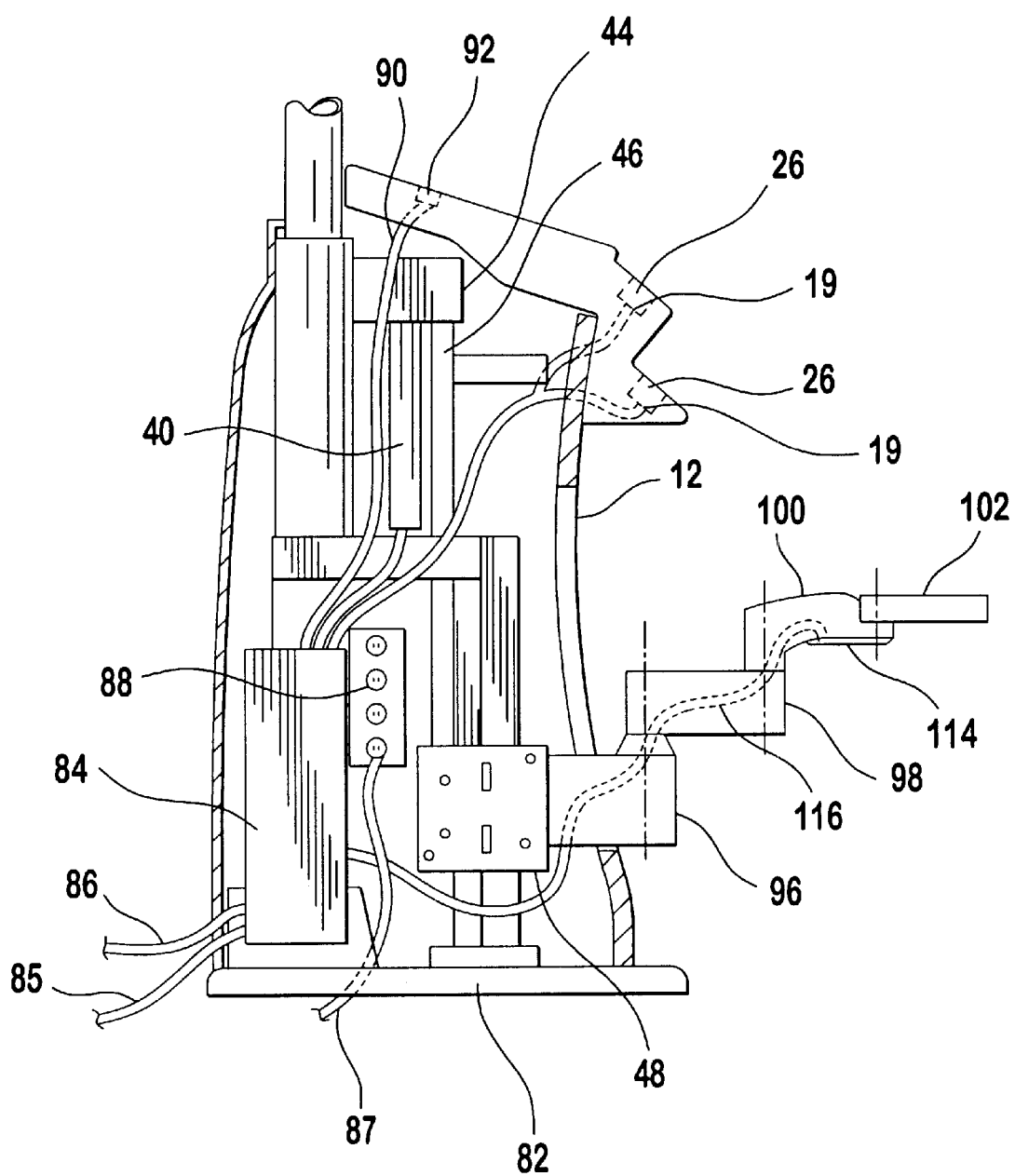
FIG. 5 is a side view of the interior of the housing showing the controller and the power supply of the instrument stand in accordance with the present invention.

The membrane switch control pad 24 is electrically connected to a controller 84 located in the interior space of the housing 12, shown in FIG. 5. The remote control 28 transmits infrared signals to an infrared sensor 92 located in the housing. The infrared sensor is electrically connected to the controller 84 via wires 90. The controller is preferably, but not limited to, a custom fabricated CB and power supply controller from Richard-Lee Company Inc., and is adapted to control at least one of, and preferably all of room light on/off functions, room light dimming functions, chair height functions, motorized arm placement functions, chair and arm memory position and return functions, slit lamp on/off and dimming control functions, recharging well functions, mode control functions, and specific procedure related tools, such as screen/mirror fixation targets which provide lighting for child attention, muscle control, and fixation control.

Figure 2:
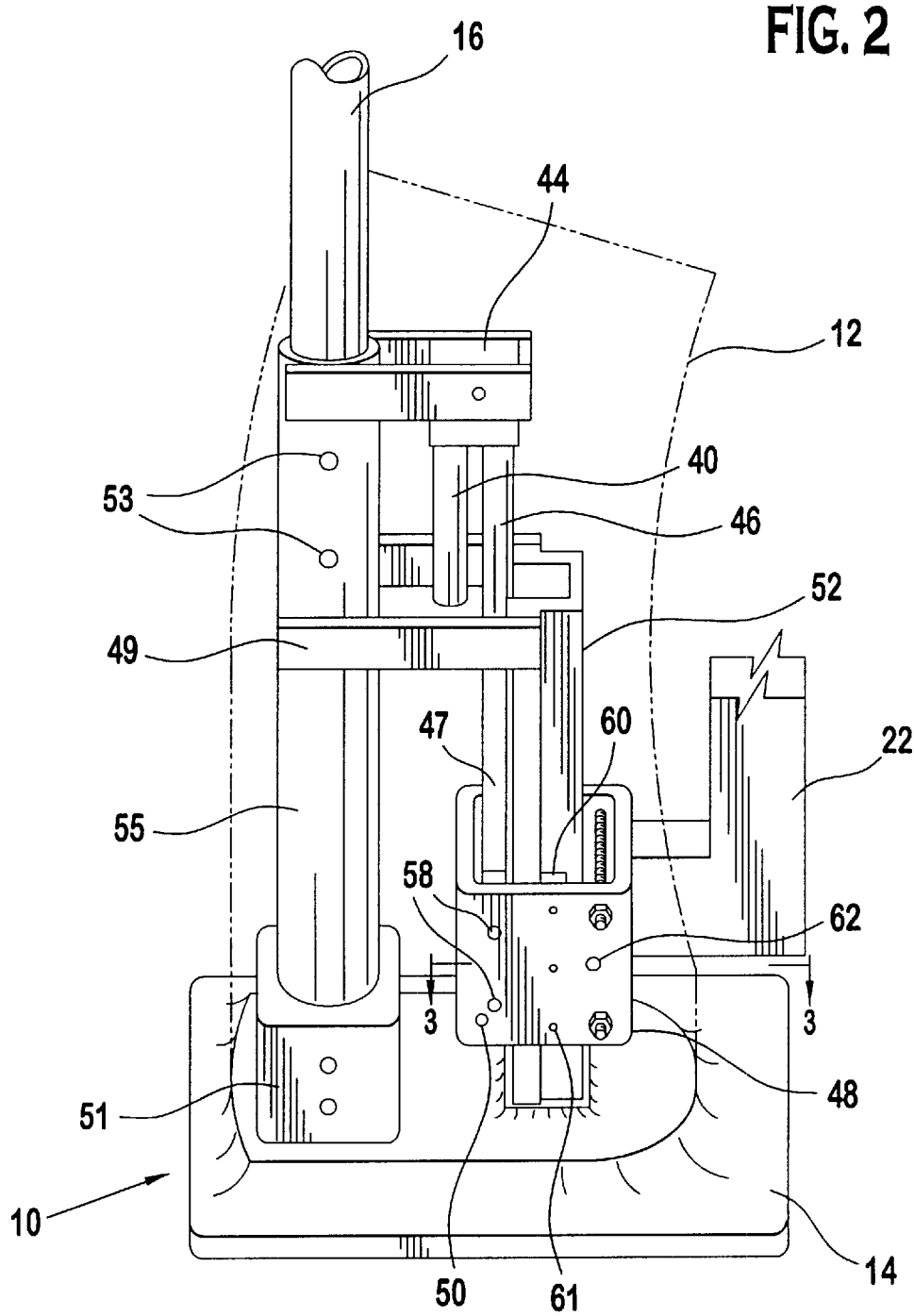
FIG. 2 is a perspective view of a side of the instrument stand of FIG. 1 with the cover removed to show a motor, a gear box, and the power actuated arm movement assembly.

Referring now to FIGS. 2 and 5, a linear actuator 46 is shown having an electric motor 40 that is connected to an electrical supply through the controller 84. The linear actuator 46 includes a gearbox 44 that is driven by the electric motor 40 to extend or retract the actuator rod 47. The electric motor 40 has at least two speeds, and may be variable speed, such that the actuator speed can be varied. In the preferred embodiment, the electric motor is completely variable from 16V to 30V, and multiple speeds could be defined, depending on the particular requirements. The actuator rod 47 extends generally vertically downward from the gear box 44 and passes through an arm support tube 48. A connecting pin 50 is used to connect the end of the actuator rod 47 to the arm support tube 48, upon which the arm 22 is attached.

Figure 3:
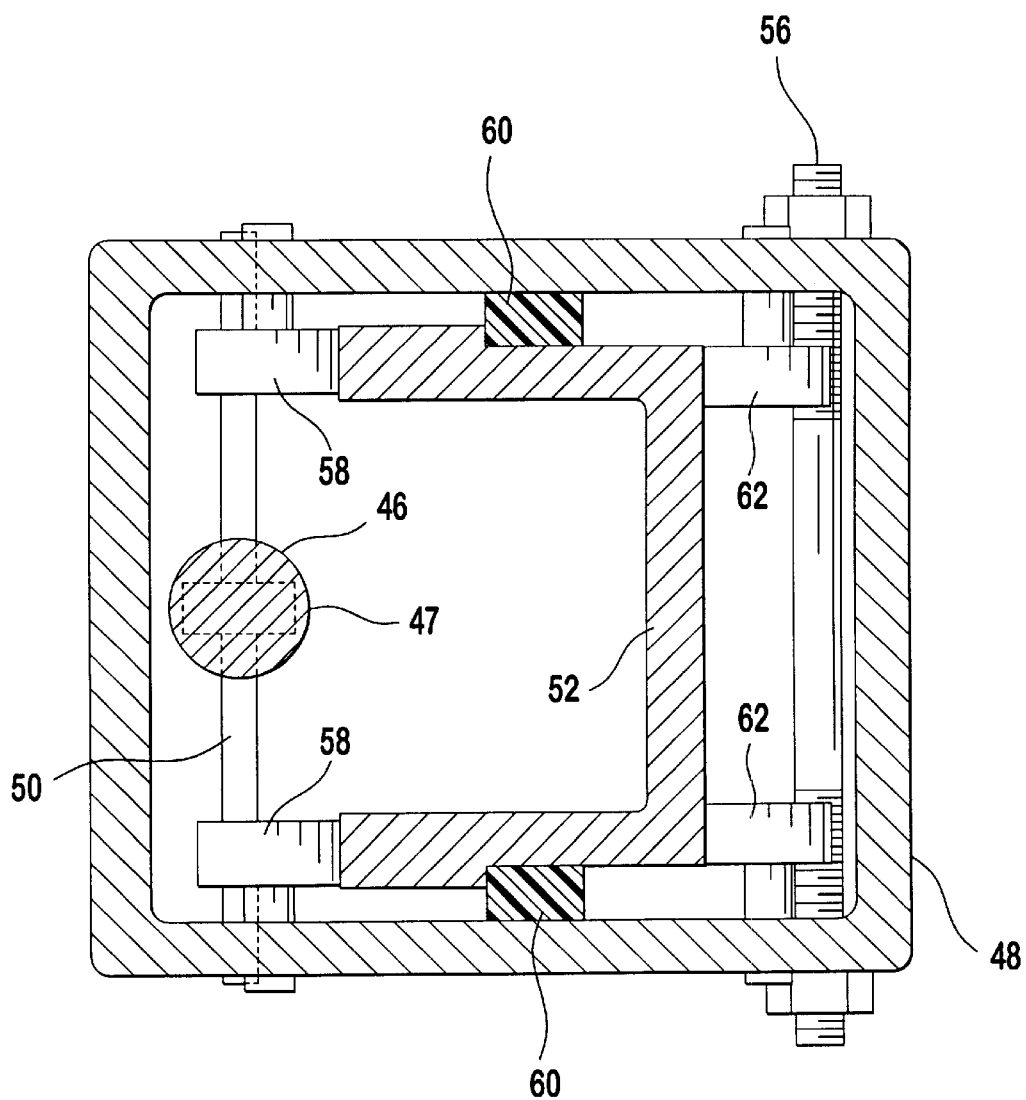
FIG. 3 is a cross-sectional view of the channel support structure for the motorized arm movement mechanism taken along line 3—3 in FIG. 2.

Referring again to FIG. 2, an arm support channel 52 is attached to the base 14 to provide a rigid structure upon which the arm support tube 48 travels. The top of the arm support channel 52 is attached by braces 49 to the support column 55 for the instrument support pole 16. As shown in FIGS. 2 and 3, the arm support tube 48 is movably supported on the arm support channel 52 by rollers 58, 62. The rollers 58, 62, which are preferably in the form of cam followers, are located on two sides of the arm support tube 48, and contact on opposing sides of the arm support channel 52. The rollers 58 contact one side of the arm support channel 52. On the opposite side of the arm support channel 52, two rollers 62 provide lateral, side-to-side support. Preferably, the roller contact surfaces on the support channel 52 are machined smooth and true to provide uniform linear guide surfaces for the rollers 58, 62. Solid glides 60 are located on the inside, front and back of the arm support tube 48. The glides 60 are preferably attached with fasteners 61, and extend the full height of the arm support tube 48 to provide for lateral front to back support, such that the motion of the arm support tube 48 is constrained to generally linear up and down movement. The solid glide is preferably made from DELRIN AF™ (DELRIN™ and a 13% TEFLON™ mixture) (DELRIN™ and TEFLON™ are trademarks of DuPont) although other suitable materials may be used. Those skilled in the art will recognize that any combination of rollers and glides may be utilized, or that all rollers or all glides could be used to limit the motion of the arm support tube 48 to up and down movement.

In the preferred embodiment, two threaded rods 56 extend through opposing sidewalls of the arm support tube 48 at the top and bottom of the arm support tube 48. The threaded rods 56 provide an adjustable tensioning between the opposing sidewalls of the arm support tube 48, adding structural rigidity. The threaded rods 56 are attached to the arm support tube 48 through washers and nuts or other appropriate mechanical fasteners placed on the external sides of the arm support tube 48.

As shown in FIG. 2, the support column 55 is attached to an additional counter-weight 51 on the base 14. Set screws 53 are installed in support column 55 to lock the instrument support pole 16 in position.

Figure 4:
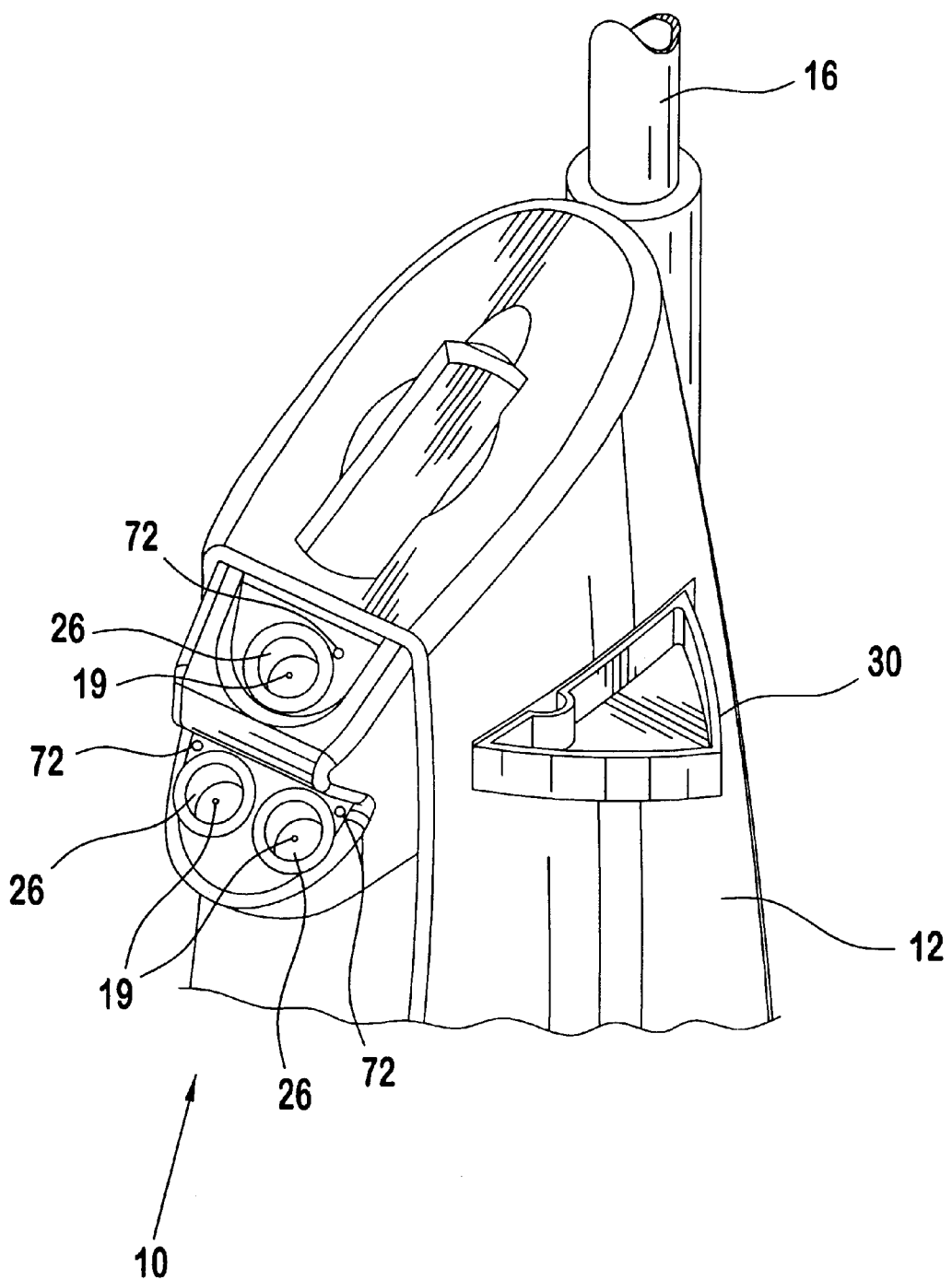
FIG. 4 is a partial perspective view, similar to FIG. 1, illustrating the recharging wells, the pop-out tray and the remote control holder of the invention.

Referring now to FIG. 4, a top view of the recharging wells 26 is shown. In the preferred embodiments, three recharging wells 26 are located generally near the top of the housing 12. However, the location and number of recharging wells can be varied, if desired. The recharging wells 26 allow for reception of rechargeable medical instruments. Recharge signal indicators 72 are placed adjacent to the recharging wells 26 to aid in identification of charging activity. Rechargeable battery medical instruments may be recharged in the recharging wells 26 by inserting the instrument into the female connection of one of the recharging wells 26. The recharging wells 26 allow for initial charging at a specific rate, such as 150 mA at 8.5V, or trickle charging, for example 15 mA at 12V, of rechargeable battery-powered medical instruments. Other charging rates could be utilized, if desired.

FIG. 5 shows the interior of the housing 12, with the controller 84 and connections to the recharging wells 26 and sensors which will be described in more detail below. An infrared sensor 92 is connected to the controller 84 through wires 90. Upon reception of signals from the remote control 28, the infrared sensor 92 transmits signals through the wires 90 to the controller 84. Control signals are also transmitted from the membrane switch control pad 24. The controller 84 is also connected to the electric motor 40 of the linear actuator 46 for actuation of the motorized arm 22. The controller 84 may be connected via cables 85, 87 to instruments used during examination, to the patient chair 11, for control of positioning functions, and to the room lighting, such that stand and room lights may be controlled by the remote control 28.

The charging wells 26 include a sensor for determining if an instrument has been removed. In the preferred embodiment, a pointed machine screw 19 extends into the recharging well 26 to act as a contact for charging and is connected to a circuit sensing control loop connected to the controller 84. When an instrument is removed, the controller 84 can automatically alter the room lighting level appropriate for the instrument which was removed.

Figure 6:
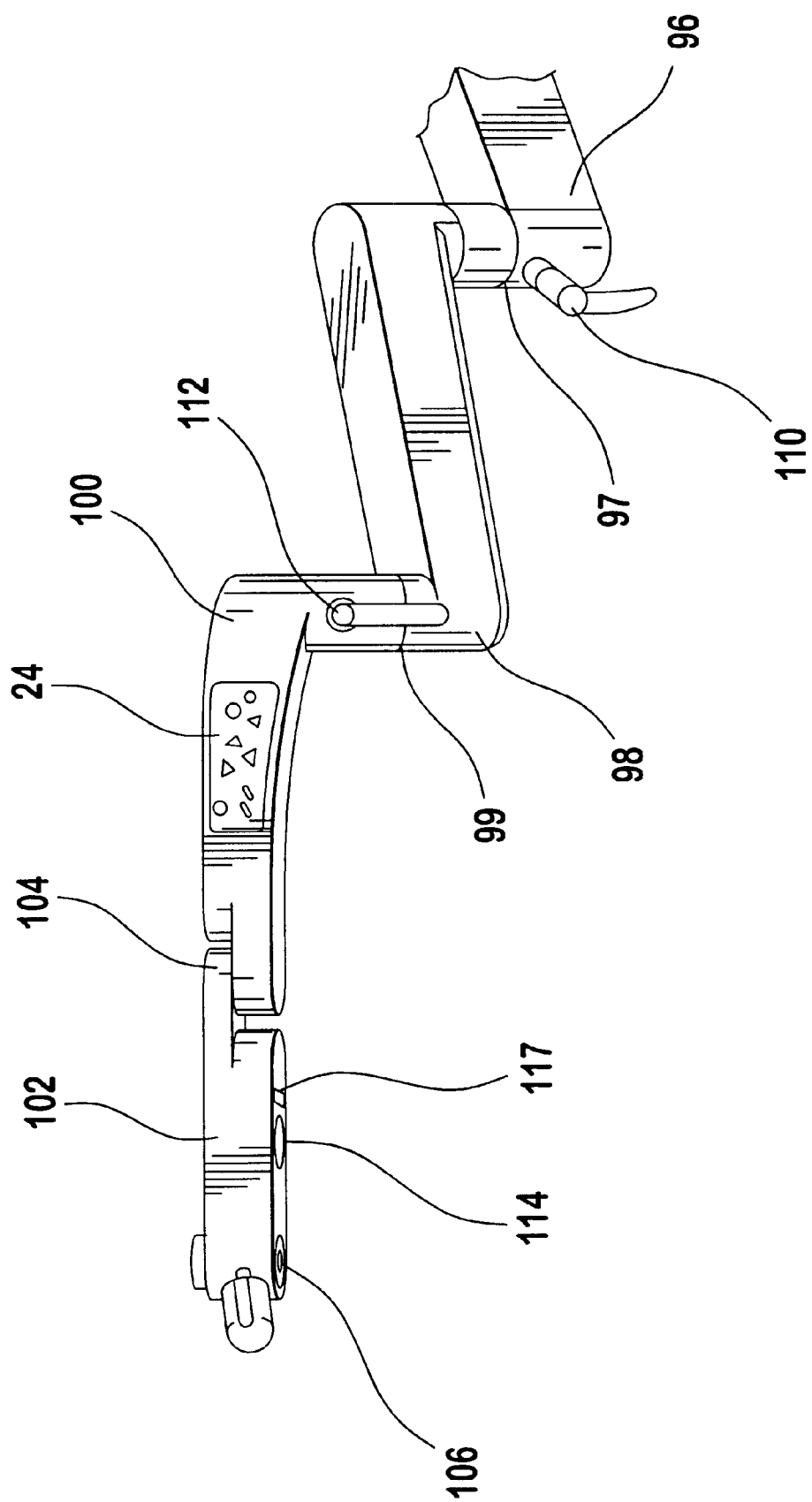
FIG. 6 is a side view of the extendable motorized arm, including an integrated membrane switch control pad and sensor, used in connection with an alternative embodiment of the present invention.

FIG. 6 shows a side view of the extendable motorized arm 22. The extendable motorized arm 22 includes the integrated membrane switch control pad 24 and a safety switch 114. A first section 96 of the motorized arm is connected to the arm support tube 48. Elevation of the arm support tube 48 will cause the motorized arm 22 to rise. A second section 98 of the motorized arm is pivotably connected to the first section 96 through a bearing 97. The first section 96 of the motorized arm has a locking handle 110 used to fix the second section 98 in position relative to the first section 96. A third section 100 of the motorized arm is pivotably connected to the second section 98 through a bearing 99. The third section 100 of the motorized arm, has a locking handle 112, to secure the third section 100 in a fixed position relative to the second section 98. The membrane switch control pad 24 is also preferably located on the third section 100 of the motorized arm. The membrane switch control pad 24 provides control functionality for slit lamp operation, arm positioning, chair positioning, speed control and memory of chair and arm positions. A fourth section 102 of the motorized arm is pivotably connected to the third section 100 by a pin 104. A shaft holder 106 is formed in the fourth section 102 of the motorized arm which allows various instruments to be installed on the motorized arm 22.

The sensor 114 is placed on the underside of the motorized arm 22 and connected to the controller 84 by a wire 116.

The sensor 114 stops movement of the motorized arm 22, preferably instantaneously, upon contact with an object on the underside of the arm. The sensor 114 may also signal the controller 84 to stop chair elevation, preferably instantaneously. This prevents potential injury to patients from the moving motorized arm 22 and/or movement of the chair 11 when the arm 22 is in position. The sensor 114 may be elongated and is preferably mounted along the bottom side of the motorized arm 22. The sensor 114 may also include a receptacle 117 for connecting additional sensors (not shown) located on the underside of equipment attached to arm, which may extend to a position lower than the arm 22.

Figure 7:
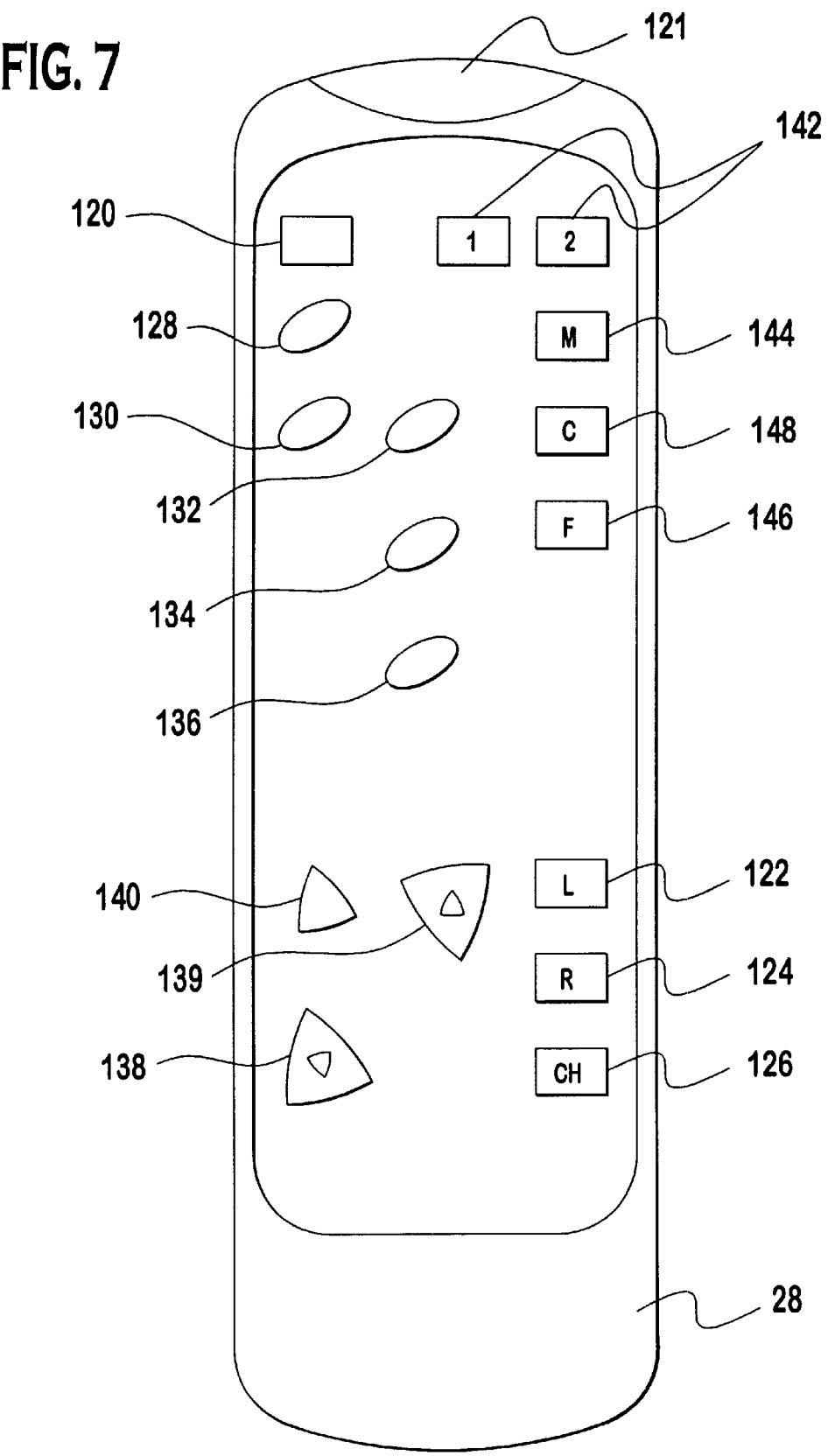
FIG. 7 is a plan view of a remote control device used in connection with the instrument stand of FIG. 1, which includes mode selection buttons for chair, overhead lamp, and room light dimming functions, incremental control buttons, screen/mirror target activation, and auto return feature buttons.

FIG. 7 shows a preferred embodiment of the infrared remote control 28 used to control instrument stand functions. An "on/off" button 120 is located on the infrared remote control 28 in order to provide on/off function capability for the instrument stand. Signals generated by the circuitry of the infrared unit, are emitted through a front IR transmissive shield 121 in the known manner. Mode control circuitry is provided in the remote control 28 in order to allow for selection between chair, lamp or room functions. A lamp mode control 122, a room light control mode 124, and a chair mode control 126 are located on the infrared remote control 28 to select between the three different functions. The remote control 28 has a lamp control "on" button 128 and a lamp control "off" button 130. A room light control "on" button 132 and a room light control "off" button 134 are also located on the unit. A dimming button 136 for room light controls is also placed on the remote control 28. Incremental control buttons 138, 139 are placed on the infrared remote control to aid in fine tuning room light dimming levels, and chair positioning. An auto return button 140 provides an automatic return feature to a preset chair location. Auxiliary circuitry buttons 142 provide signals to the controller 84 to activate and deactivate power to internal outlets. External instruments may be connected and programmed to turn on automatically. A muscle control button 144, a child attention button 148, and a fixation control button 146 are placed on the remote control to activate screen/mirror fixation target light features during the eye examination process. The buttons are used to generate an electrical signal in the remote control 28 that is converted to an infrared signal and transmitted in a known manner. These IR signals are received by the IR sensor 92 or other IR sensors which are connected to the controller 84. Those skilled in the art will recognize that other buttons for other functions may be provided based on particular applications. Controls 120, 122, 124, 126, 128, 130, 132, 134, 136, 138, 139, 140, 142, 144, 146, and 148 on the remote control 28 have user descriptive markings which are identifiable in low light. The markings preferably are formed from a material which glows in the dark, and may include raised indicia to provide a tactile means of identification.

Figure 8:
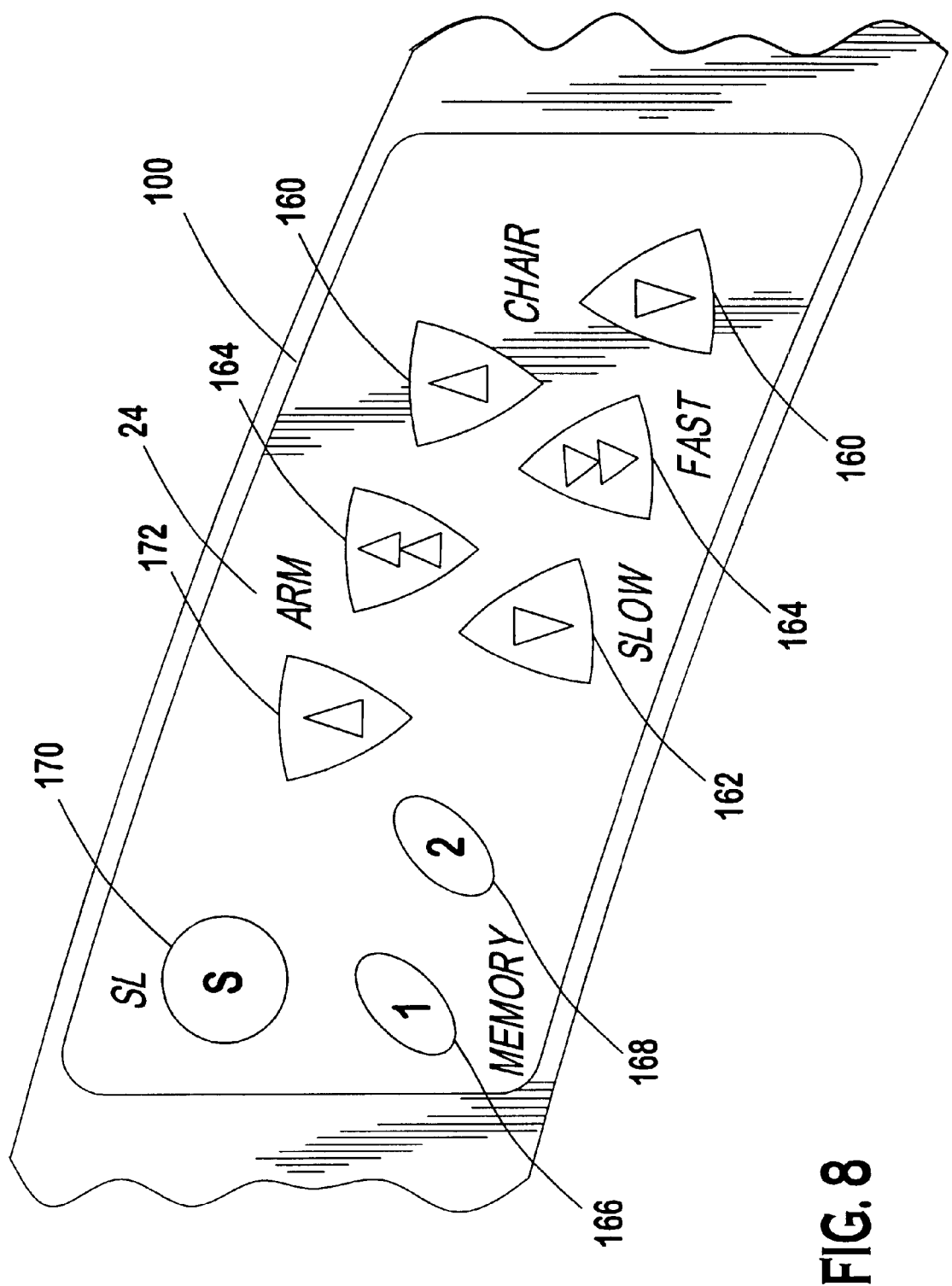
FIG. 8 is an enlarged side view of the membrane switch control pad on the motorized arm shown in FIG. 6.

Referring now to FIG. 8, the membrane switch control pad 24 is shown in detail. The membrane switch control pad 24 includes chair positioning circuitry, slit lamp controls, arm controls and memory buttons. Chair position height control buttons 160 allow the operator to reposition the chair to a desired height. A motorized arm raising button 172 and a motorized arm lowering button 162 are located for operator convenience. The motorized arm 22 may be positioned at a faster rate using the fast buttons 164. Two memory buttons 166 and 168 are located on the membrane switch control pad 24 to enable the controller 84 to store stand arm height settings in the memory of the controller 84 for recall at a later time so that the motorized arm 22 can be easily returned to a predetermined position. A slit lamp control button 170 is also placed on the motorized arm membrane switch control panel 24.

As shown in FIGS. 1 and 4, a pop-out tray 30 is provided in the external housing for storing objects in the stand. The pop-out tray 30 has a generally flush exterior face when placed in the closed position, and pivots about a single hinge point to an open position, as shown in FIG. 4.

While the invention has been described in detail on the basis of the preferred embodiments, the invention is not limited to the specific embodiments described above, which should be considered as merely exemplary. Further modifications and extensions of the present invention may be developed based upon the foregoing, and all such modifications are deemed to be within the scope of the present invention as defined by the claims.

What is claimed is:

1. A medical stand comprising:
   a housing defining an interior space;
   a control signaling device adapted to control at least one of a lamp circuit, screen/mirror fixation targets, internal outlets, room lights, a positioning circuit for a chair, and an arm position circuit;
   a controller located in the interior space in communication with the control signaling device;
   an electric motor in electrical communication the controller;
   an actuator connected to the electric motor;
   a motor driven arm extending from a side opening in the housing connected to the actuator, whereby the arm can be positioned up and down and fixed in position independent of a weight on the arm without the requirement for moving counterbalance weights; and
   a sensor on the motor driven arm connected to the controller adapted to stop movement of at least one of the motor driven arm and the chair upon contact with an object.

2. The medical stand of claim 1, wherein the control signaling device comprises a remote control adapted to transmit control signals and a receiving sensor connected to the controller.

3. The medical stand of claim 1, further comprising:
   a base connected to a bottom of the external housing, the base having a non-skid surface which rests upon a floor.

4. The medical stand of claim 1, further comprising:
   a storage tray connected to the housing, the tray being movable between a closed position, in which an outer surface of the tray fits approximately flush with the housing, and an open position.

5. The medical stand of claim 1, wherein the motor has multiple speeds.

6. The medical stand of claim 1, wherein the control signaling device further comprises:
   user descriptive markings that are low light identifiable.

7. The medical stand of claim 1, wherein the control signaling device comprises:
   a fixed control pad located on the arm; and
   a remote control adapted to control at least one of a stand control on-off circuit, a room light control circuit, a mode control circuit for switching between lamp, chair and room light functions, and an incremental control circuit for use with the lamp, chair and room light circuits.

8. The medical stand of claim 7, wherein the control signaling device further comprises:
   an automatic control adapted to transmit a signal to the controller to place the arm into one of a plurality of predetermined positions.

9. The medical stand of claim 1, wherein the motor driven arm comprises:

a first arm member connected to the actuator, the actuator driven by the motor to adjust a height of the first member.

10. The medical stand of claim 9, wherein the control signaling device is located on the motor driven arm, and includes:

an arm movement speed control circuit and a circuit to enable room light dimming upon slit lamp activation, both of which interface with the controller.

11. The medical stand of claim 10, wherein the controller further comprises:

a memory adapted to store user defined input data, the control signaling device including a control adapted to signal the controller to move the arm to an arm placement position using the stored data.

12. The medical stand of claim 9, wherein the motor driven arm further comprises:

a second arm member pivotally connected to the first arm member;

the first and second arm members being securable in fixed relative positions by a locking device.

13. The medical stand of claim 12, wherein the motor driven arm further comprises:

a third arm member having a first and a second end, the first end of the third arm member is pivotally connected to the second arm member, the second end of the third arm member being adapted to support medical instruments.

14. The medical stand of claim 1, further comprising:

at least one outlet well having a rechargeable power source charging circuit adapted to receive and charge a medical instrument.

15. The medical stand of claim 14, wherein the rechargeable power source charging circuit is variable.

16. The medical stand of claim 14, further comprising:

a sensor connected to the controller adapted to sense input or removal of medical instruments in the at least one outlet well, that causes the controller to alter a room lighting level upon instrument removal.

17. The medical stand of claim 1, further comprising:

a lamp controlled by the lamp control circuit; and a refractor arm supported from a support pole.

* * * * *

UNITED STATES PATENT AND TRADEMARK OFFICE
CERTIFICATE OF CORRECTION

PATENT NO. : 6,575,575 B2
DATED : June 10, 2003
INVENTOR(S) : O'Brien et al.

It is certified that error appears in the above-identified patent and that said Letters Patent is hereby corrected as shown below:

Column 6,
Line 25, after the word "communication", insert the word -- with --.

Signed and Sealed this

Seventh Day of October, 2003

JAMES E. ROGAN
*Director of the United States Patent and Trademark Office*